United States Patent
Kim et al.

(10) Patent No.: US 12,354,270 B2
(45) Date of Patent: Jul. 8, 2025

(54) MEDICAL IMAGE PROCESSING METHOD FOR PROCESSING PEDIATRIC SIMPLE X-RAY IMAGE USING MACHINE LEARNING MODEL AND MEDICAL IMAGE PROCESSING APPARATUS THEREFOR

(71) Applicant: PROMEDIUS INC., Seoul (KR)

(72) Inventors: Namkug Kim, Seoul (KR); Kyung Jin Cho, Seoul (KR); Mingyu Kim, Seoul (KR); Ji Yeon Suh, Hwaseong-si (KR); Gil-Sun Hong, Seoul (KR)

(73) Assignee: PROMEDIUS INC., Seoul (KR)

( * ) Notice: Subject to any disclaimer, the term of this patent is extended or adjusted under 35 U.S.C. 154(b) by 403 days.

(21) Appl. No.: 18/168,400

(22) Filed: Feb. 13, 2023

(65) Prior Publication Data
US 2023/0260123 A1     Aug. 17, 2023

(30) Foreign Application Priority Data
Feb. 15, 2022    (KR) .................. 10-2022-0019819

(51) Int. Cl.
*G06K 9/00*   (2022.01)
*G06T 5/50*   (2006.01)
(Continued)

(52) U.S. Cl.
CPC ............. *G06T 7/0014* (2013.01); *G06T 5/50* (2013.01); *G16H 30/40* (2018.01);
(Continued)

(58) Field of Classification Search
CPC ............. G06T 7/0014; G06T 5/50; G06T 2207/10012; G06T 2207/10081;
(Continued)

(56) References Cited

U.S. PATENT DOCUMENTS 11,158,050 B2 *   10/2021   Huo .................. G06T 7/0014
2018/0042565 A1 *   2/2018   Wilson .................. A61B 6/541
(Continued)

FOREIGN PATENT DOCUMENTS

KR    10-2018-0059329 A    6/2018

OTHER PUBLICATIONS

Dong Yul Oh, Il Dong Yun, Learning Bone Suppression from Dual Energy Chest X-rays using Adversarial Networks, Computer Science > Computer Vision and Pattern Recognition, Nov. 5, 2018, arXiv:1811.02628 [cs.CV], https://doi.org/10.48550/arXiv.1811.02628 (Year: 2018).*
(Continued)

*Primary Examiner* — Atiba O Fitzpatrick
(74) *Attorney, Agent, or Firm* — Studebaker Brackett PLLC

(57) ABSTRACT

A medical image processing method for processing a pediatric simple X-ray image using a machine learning model and a medical image processing apparatus therefor are provided. The apparatus applies a style conversion model to a CT image pair including a basic CT image and a suppression CT image where at least a portion of a bone of the basic CT image is suppressed to convert the CT image pair into a conversion image pair and trains a bone suppression model for a simple X-ray image based on training data including the conversion image pair.

13 Claims, 6 Drawing Sheets

(51) Int. Cl.
*G06T 7/00* (2017.01)
*G16H 30/40* (2018.01)

(52) U.S. Cl.
CPC ............... *G06T 2207/10012* (2013.01); *G06T 2207/10081* (2013.01); *G06T 2207/10116* (2013.01); *G06T 2207/20081* (2013.01); *G06T 2207/30008* (2013.01); *G06T 2207/30061* (2013.01); *G06T 2207/30168* (2013.01)

(58) Field of Classification Search
CPC . G06T 2207/10116; G06T 2207/20081; G06T 2207/30008; G06T 2207/30061; G06T 2207/30168; G06T 5/60; G06T 5/94; G06T 2207/20084; G06T 2207/30048; G06T 2211/441; G06T 11/008; G06T 2207/30012; G06T 2207/10124; G06T 3/00; G06T 3/02; G06T 3/073; G16H 30/40; A61B 6/5252; A61B 6/02; A61B 6/03; A61B 6/032; A61B 2090/3762; A61B 2090/376; G06N 3/0475; G06V 10/774; G06F 18/214
See application file for complete search history.

(56) References Cited

U.S. PATENT DOCUMENTS

| | | | | |
|---|---|---|---|---|
| 2018/0116620 | A1* | 5/2018 | Chen | G06T 7/136 |
| 2020/0380680 | A1* | 12/2020 | Aoyagi | G06V 10/772 |
| 2020/0410673 | A1* | 12/2020 | Baltruschat | G06V 10/764 |
| 2021/0030374 | A1* | 2/2021 | Takahashi | A61B 6/504 |
| 2021/0212641 | A1 | 7/2021 | Song et al. | |
| 2021/0398254 | A1* | 12/2021 | Oshikawa | G06N 20/00 |
| 2023/0149092 | A1* | 5/2023 | Fouts | G06N 3/0464 |
| | | | | 600/300 |
| 2024/0122556 | A1* | 4/2024 | Hiasa | A61B 6/5235 |

OTHER PUBLICATIONS

Terunuma, T., Tokui, A. & Sakae, T. Novel real-time tumor-contouring method using deep learning to prevent mistracking in X-ray fluoroscopy. Radiol Phys Technol 11, 43-53 (2018). https://doi.org/10.1007/s12194-017-0435-0 (Year: 2018).*

Kyungjin Cho et al., Bone suppression on pediatric chest radiographs via a deep learning-based cascade model, Computer Methods and Programs in Biomedicine, vol. 215, pp. 1-9, Jan. 7, 2022.

A Notice of Allowance mailed by the Korean Intellectual Property Office on Jan. 4, 2023, which corresponds to Korean Patent Application No. 10-2022-0019819 with English language translation.

Naoki Matsubara et al., Bone suppression for chest X-ray image using a convolutional neural filter, Australasian Physical & Engineering Sciences in Medicine, pp. 1-12, Nov. 26, 2019.

Han Li, et al., High-Resolution Chest X-Ray Bone Suppression Using Unpaired CT Structural Priors, IEEE Transactions on Medical Imaging, vol. 39, Issue: 10, pp. 1-11, Mar. 29. 2020.

Afonso U. Fonseca, et al., Pediatric chest radiography research agenda: Is deep learning still in childhood, arXiv preprint arXiv, pp. 1-18, Oct. 2020.

Yunbi Liu, et al., Generating Dual-Energy Subtraction Soft-Tissue Images from Chest Radiographs via Bone Edge-Guided GAN, MICCAI, pp. 678-687, 2020.

* cited by examiner

MEDICAL IMAGE PROCESSING METHOD FOR PROCESSING PEDIATRIC SIMPLE X-RAY IMAGE USING MACHINE LEARNING MODEL AND MEDICAL IMAGE PROCESSING APPARATUS THEREFOR

CROSS-REFERENCE TO RELATED APPLICATIONS

A claim for priority under 35 U.S.C. § 119 is made to Korean Patent Application No. 10-2022-0019819 filed on Feb. 15, 2022 in the Korean Intellectual Property Office, the entire contents of which are hereby incorporated by reference.

BACKGROUND

Embodiments of the inventive concept described herein relate to a medical image processing method, and more particularly, relate to a medical image processing method for processing a pediatric simple X-ray image using a machine learning model and a medical image processing apparatus therefor.

Image processing has been applied in many various fields after it was applied to transmission photography in the 1920s. Particularly, medical image processing began with its application to a simple X-ray image, and in the 1970s, with the development of various medical imaging devices such as computed tomography, magnetic resonance tomography, ultrasound diagnosis, single photon emission computed tomography, and positron emission tomography, the importance is increasing day by day. Such medical imaging devices enable the synthesis of 3D stereoscopic images of the internal organs of the human body by providing tomographic images of the human body, and many studies are being conducted in various fields such as virtual surgery simulation to reduce the risk of surgery in conjunction with virtual reality. Recently, interest in automatic diagnosis through image information processing as well as visualization, for example, 3D image synthesis, virtual surgery simulation, or the like, has been greatly increased, and the field of computer-assisted diagnosis has been actively researched. Particularly, research has been conducted in various application fields, such as automatic detection of lung tumors for early diagnosis of lung cancer, extraction of variations over time in images, measurement of lung volume for lung function tests, and measurement of body fat for obesity tests.

Meanwhile, despite the fact that computed tomography and magnetic resonance tomography provide better information by providing tomography images, because it is inexpensive and convenient to capture in X-ray simple capturing, the X-ray simple capturing is widely used for early diagnosis such as regular checkups or screening of diseases. However, X-ray tomography images are projected images. Organs are not clearly distinguished in the X-ray tomography images, and images vary greatly and are often unclear depending on capturing conditions, so there are many difficulties in image processing in the X-ray tomography images and the X-ray tomography is an area where research has not been active compared to computed tomography or magnetic resonance tomography.

Nevertheless, research on image processing in chest X-ray images has been conducted for a long time. Recently, studies on image processing of chest X-ray images have been actively conducted to find abnormal parts of the lungs, such as early diagnosis of lung cancer, and to find out changes over time. Furthermore, from image processing that helps readout by improving the quality of images by increasing contrast and reducing noise in unclear chest X-ray images that are difficult to read, to image processing that helps diagnosis by finding abnormal parts such as lung cancer and lung tumors, research has been conducted in various ways.

However, in chest X-ray images, the quality of images varies greatly depending on the amount of the X-ray, the intensity of the X-ray, capturing conditions, patient's posture, breathing, development conditions, and the like and it is difficult to obtain useful information through image processing because anatomical structures are complicatedly intertwined.

SUMMARY

According to an embodiment, a method may include obtaining a basic computer tomography (CT) image and a suppression CT image where at least a portion of a bone of the basic CT image is suppressed, applying a style conversion model to a CT image pair including the basic CT image and the suppression CT image to convert the CT image pair into a conversion image pair, and training a bone suppression model for a simple X-ray image based on training data including the conversion image pair. The obtaining of the basic CT image and the suppression CT image may include projecting a basic stereoscopic CT image onto a reference plane to obtain the basic CT image being a planar CT image and projecting a suppression stereoscopic CT image onto the reference plane to obtain the suppression CT image being a planar CT image, the suppression stereoscopic CT image being obtained by changing a first voxel value corresponding to at least a portion of a bone of the basic stereoscopic CT image to a second voxel value corresponding to a non-bone, the at least a portion of the bone being a bone corresponding to a voxel having the first voxel value which belongs to a threshold range in the bone of the basic stereoscopic CT image, and the second voxel value being a value of a voxel corresponding to the non-bone within a threshold distance from a voxel having the first voxel value. The training of the bone suppression model may include applying the bone suppression model to a basic conversion image of the conversion image pair to obtain a training output image, calculating an objective function value of the bone suppression model based on the training output image and a suppression conversion image of the conversion image pair, and updating parameters of the bone suppression model using the objective function value. The calculating of the objective function value may include calculating the objective function value based on a pixel value difference between a first pixel of the training output image and a second pixel of the suppression conversion image, the second pixel corresponding to the first pixel, the objective function value being calculated as a large value as the pixel value difference increases. The obtaining of the training output image, the calculating of the objective function value, and the updating of the parameters may be repeated to train the bone suppression model, until the objective function value is less than a predetermined threshold.

Furthermore, the method may further include applying the trained bone suppression model to a simple X-ray input image to obtain a simple X-ray output image where at least a portion of a bone of the simple X-ray input image is suppressed. In this case, the obtaining of the simple X-ray output image may include applying the bone suppression model to the simple X-ray input image for pediatrics to obtain the simple X-ray output image where the at least a portion of the bone of the simple X-ray input image is suppressed.

Furthermore, the method may further include obtaining the CT image pair for pediatrics, the CT image pair including the basic CT image and the suppression CT image for the pediatrics.

Furthermore, the converting into the conversion image pair may include applying the style conversion model to the CT image pair for pediatrics to convert the CT image pair for the pediatrics into the conversion image pair for the pediatrics.

Furthermore, the training of the bone suppression model may include using a basic conversion image of the conversion image pair of the training data as a training input image and using a suppression conversion image of the conversion image pair as a ground truth output image to train the bone suppression model by means of supervised learning.

According to an embodiment, an apparatus may include a processor that obtains a basic CT image and a suppression CT image where at least a portion of a bone of the basic CT image is suppressed, applies a style conversion model to a CT image pair including the basic CT image and the suppression CT image to convert the CT image pair into a conversion image pair, and trains a bone suppression model for a simple X-ray image based on training data including the conversion image pair. The processor may project a basic stereoscopic CT image onto a reference plane to obtain the basic CT image being a planar CT image, when obtaining the basic CT image and the suppression CT image, and may project a suppression stereoscopic CT image onto the reference plane to obtain the suppression CT image being a planar CT image, the suppression stereoscopic CT image being obtained by changing a first voxel value corresponding to at least a portion of a bone of the basic stereoscopic CT image to a second voxel value corresponding to a non-bone, the at least a portion of the bone being a bone corresponding to a voxel having the first voxel value which belongs to a threshold range in the bone of the basic stereoscopic CT image, and the second voxel value being a value of a voxel corresponding to the non-bone within a threshold distance from a voxel having the first voxel value, may apply the bone suppression model to a basic conversion image of the conversion image pair to obtain a training output image, when training the bone suppression model, may calculate an objective function value of the bone suppression model based on the training output image and a suppression conversion image of the conversion image pair, and may update parameters of the bone suppression model using the objective function value, may calculate the objective function value based on a pixel value difference between a first pixel of the training output image and a second pixel of the suppression conversion image, the second pixel corresponding to the first pixel, when calculating the objective function value, the objective function value being calculated as a large value as the pixel value difference increases, and may repeat the obtaining of the training output image, the calculating of the objective function value, and the updating of the parameters to train the bone suppression model, until the objective function value is less than a predetermined threshold.

The processor according to the inventive concept may apply the trained bone suppression model to a simple X-ray input image to obtain a simple X-ray output image where at least a portion of a bone of the simple X-ray input image is suppressed. In other words, the processor according to the inventive concept may apply the bone suppression model to the simple X-ray input image for pediatrics to obtain the simple X-ray output image where the at least a portion of the bone of the simple X-ray input image is suppressed.

Furthermore, the processor according to the inventive concept may obtain the CT image pair for pediatrics, the CT image pair including the basic CT image and the suppression CT image for the pediatrics.

Furthermore, the processor according to the inventive concept may apply the style conversion model to the CT image pair for pediatrics to convert the CT image pair for the pediatrics into the conversion image pair for the pediatrics.

Furthermore, the processor according to the inventive concept may use a basic conversion image of the conversion image pair of the training data as a training input image and may use a suppression conversion image of the conversion image pair as a ground truth output image to train the bone suppression model by means of supervised learning.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
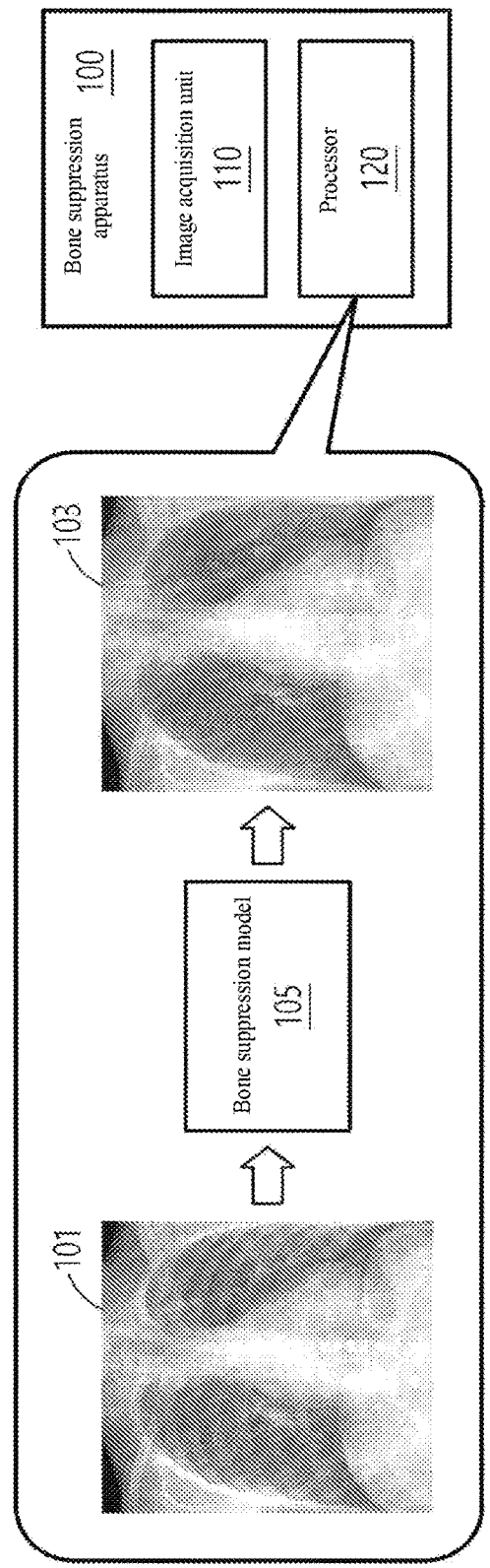
FIG. 1 illustrates an operation of a bone suppression apparatus according to the inventive concept.

Specific structural or functional descriptions of embodiments of the inventive concept are disclosed for illustrative purposes only, and may be modified and implemented in various forms. Thus, the form actually implemented is not limited only to a specific embodiment disclosed, and the scope of the specification includes changes, equivalents, or substitutes included in the technical ideal described in embodiments.

The terms "first" or "second" are used to describe various components, but it should be interpreted that the terms are only used to distinguish one component from other components. For example, a first component may be termed a second component, and similarly, a second component may be termed a first component.

When a component is referred to as being or "coupled" to another component, it is understood that it may be directly connected or coupled to the other component, but other components may exist in the middle.

Singular expressions include plural expressions unless the context clearly indicates otherwise. In the specification, it is to be understood that terms such as "comprise" or "have" are intended to designate that the specified features, numbers, steps, operations, components, parts, or combinations thereof exist, but do not previously preclude the possibility of the presence or addition of one or more other features, numbers, steps, operations, components, parts, or combinations thereof.

Unless otherwise defined, all terms (including technical and scientific terms) used herein have the same meaning as commonly understood by one of ordinary skill in the art. It will be further understood that terms in common usage should also be interpreted as is customary in the relevant art and not in an idealized or overly formal sense unless expressly so defined herein.

Hereinafter, embodiments will be described in detail with reference to the accompanying drawings. In the description with reference to the accompanying drawings, the same reference numerals are given to the same components regardless of reference numerals, and a duplicated description thereof will be omitted.

FIG. 1 illustrates an operation of a bone suppression apparatus according to the inventive concept.

A bone suppression apparatus 100 may be an apparatus for processing a simple X-ray image, which may output an output image 103 where at least a portion of a bone of an input image 101 is suppressed.

The simple X-ray image may be a planar image, and may indicate an image obtained by transmitting an X-ray emitted from an X-ray source to a target and detecting a difference in strength of the transmitted X-ray at a detector. The simple X-ray image may be used to identify an internal structure of the target and/or diagnose the target. The internal structure of the target may be identified based on an attenuation rate of the X-ray, which varies with density of the target and/or an atomic number of an atom constituting the target.

A pixel value of the simple X-ray image may refer to the attenuation rate of the X-ray by at least one of a bone, an organ, tissue, water, fat, and air. An X-ray attenuation rate for a bone may be greater than an X-ray attenuation rate for internal soft tissue (e.g., an organ and/or tissue), water, fat, and air. Thus, when an organ and/or tissue and a bone are overlapped and represented on the simple X-ray image, a pixel value of the overlapped area may be determined predominantly by a bone with a large attenuation rate compared to an organ and/or tissue with an attenuation rate smaller than the bone. An area where an organ and/or tissue are/is overlapped with a bone in the simple X-ray image may not be suitable for observing the organ and/or the tissue.

When it is required to more observe an organ and/or tissue than a bone, an image (e.g., the output image 103) where the bone is suppressed may be used. The image where the bone is suppressed may indicate an image where the expression of the bone is limited (e.g., omitted, reduced, replaced, or the like). The image where the bone is suppressed may indicate an image where the bone is represented to be similar to a non-bone. The image where the bone is suppressed may indicate an image where a bone area changes to a non-bone area. For example, the image where the bone is suppressed may indicate an image where the bone area is changed based on a non-bone area around the bone area (e.g., a non-bone area within a threshold distance from the bone area). The bone suppression apparatus 100 (e.g., an electronic device) may replace a pixel value of the bone area with a pixel value of the non-bone area in an image and may change the pixel value of the non-bone area to the same or similar value, thus generating an image where a bone is suppressed. A pixel value of a portion where a bone is suppressed in an image where expression of the bone is limited may have a value less than a difference between the pixel value of the non-bone area and a threshold pixel value. However, the inventive concept is not limited thereto. The bone suppression apparatus 100 may reduce a size and/or an area of the bone area, thus generating an image where the bone is suppressed.

The pixel value of the image where the bone is suppressed may refer to an attenuation rate by a non-bone (e.g., an organ, tissue, water, fat, air, or the like) where an attenuation rate of the X-ray by a bone in the corresponding area is limited. A pixel value of an area corresponding to the bone of the image where the bone is suppressed may be changed by removing an attenuation rate of the X-ray by the bone or replacing the attenuation rate of the X-ray with an attenuation rate by the non-bone around the area.

The image where the bone is suppressed is mainly and illustratively described for the planar image, but not limited thereto. It will be described below, but the image where the bone is suppressed may include a stereoscopic image where the bone is suppressed as a stereoscopic image (e.g., a stereoscopic CT image). A voxel value of the stereoscopic image where the bone is suppressed may refer to an attenuation rate by a non-bone where the attenuation rate of the X-ray by the bone is limited. For example, a voxel value of an area corresponding to the bone of the stereoscopic image where the bone is suppressed may be changed by removing the attenuation rate of the X-ray by the bone or replacing the attenuation rate of the X-ray with the attenuation rate by the non-bone around the area.

The bone suppression apparatus 100 according to the inventive concept may include an image acquisition unit 110, a processor 120, and a memory (not shown).

The image acquisition unit 110 may obtain and deliver an input image which is a simple X-ray image to the processor 120. For example, the image acquisition unit 110 may directly capture and obtain the simple X-ray input image 101 and may receive the simple X-ray input image 101 from the outside through an input interface.

The processor 120 may generate the simple X-ray output image 103 where at least a portion of the bone of the simple X-ray input image 101 is suppressed. The processor 120 may apply a bone suppression model 105 to the simple X-ray input image 101 to obtain the simple X-ray output image 103. The bone suppression model 105 may indicate a machine learning model learned to obtain the simple X-ray output image 103 from the simple X-ray input image 101.

The simple X-ray output image 103 may indicate a simple X-ray image, which may indicate an image processed such that a factor (e.g., another organ or a bone) which interferes with the observation of an organ and/or tissue to be observed in the simple X-ray input image 101 is not represented to increase visibility of the organ and/or tissue. The simple X-ray output image 103 may indicate an image where at least a portion of the bone of the simple X-ray input image 101 is suppressed. The simple X-ray output image 103 may indicate an image where a pixel value corresponding to at least a portion of the bone of the simple X-ray input image 101 changes to a pixel value corresponding to the non-bone. Illustratively the simple X-ray input image 101 may include a simple X-ray image obtained by capturing a chest of the patient. The bone suppression model 105 may include a machine learning model learned to output the simple X-ray output image 103 where ribs are suppressed to increase visibility of an organ and/or tissue (e.g., a lung or a heart) of the chest by being applied to a chest simple X-ray image.

The bone suppression apparatus 100 may obtain a simple X-ray image (e.g., the simple X-ray output image 103) where the bone is suppressed based on one simple X-ray image (e.g., the simple X-ray input image 101) using the bone suppression model 105. Illustratively, the bone suppression apparatus 100 may apply the bone suppression model 105 to a simple X-ray input image for pediatrics. The bone suppression apparatus 100 may obtain a simple X-ray output image where at least a portion of a bond of the simple X-ray input image for the pediatrics is suppressed.

The bone suppression apparatus 100 according to the inventive concept may obtain a simple X-ray image where at least a portion of a bone for pediatrics is suppressed as well as a simple X-ray image where at least a portion of a bone for an adult is suppressed.

The capturing of the simple X-ray image by means of a dual energy X-ray may be used to obtain a simple X-ray image where a bone is suppressed. It may be possible to capture a simple X-ray image for an adult by means of the dual energy X-ray, but it may be impossible to capture a simple X-ray image for pediatrics by means of the dual energy X-ray because the pediatrics is different in a radiation dose from the adult. Thus, unlike the adult, for pediatrics, it may be impossible to obtain a simple X-ray image where a bone is suppressed, using the capturing of the simple X-ray image by means of the dual energy X-ray.

For pediatrics as well as the adult, the simple X-ray input image 101 may be obtained by means of a single energy X-ray. Even when it is impossible to capture the simple X-ray image by means of the dual energy X-ray, by using the bone suppression apparatus 100 according to the inventive concept, the simple X-ray output image 103 where the bone is suppressed may be obtained based on the simple X-ray input image 101 obtained by means of the single energy X-ray. The bone suppression apparatus 100 according to the inventive concept may be applied to the simple X-ray input image 101 for pediatrics to obtain the simple X-ray output image 103 where at least a portion of a bond for the pediatrics is suppressed.

Training data of the bone suppression model 105 may include a training input image and a ground truth output image. For an adult, it may be possible to directly obtain the training input image and the ground truth output image by means of the dual energy X-ray. However, as described above, because it is impossible to obtain a simple X-ray image for pediatrics by means of the dual energy X-ray, another method for obtaining a training input image and a ground truth output image for the pediatrics may be required.

Hereinafter, a description will be given below of acquisition of training data of a bone suppression model and training of the bone suppression model with reference to FIGS. 2 to 6.

Figure 2:
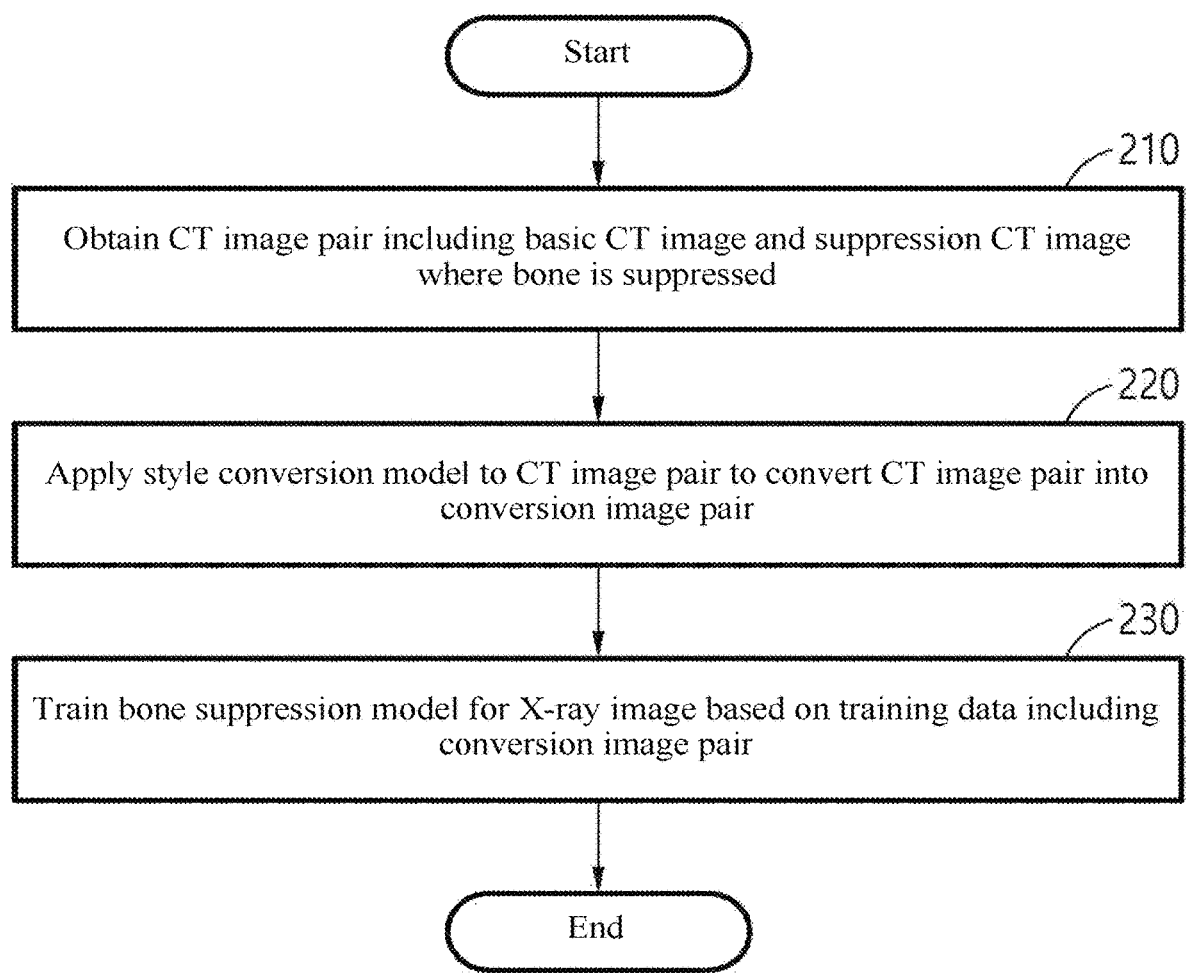
FIG. 2 illustrates an operation of a training device according to the inventive concept.

FIG. 2 illustrates an operation of a training device according to the inventive concept.

The training device according to the inventive concept may include a device which performs training of a bone suppression model (e.g., a bone suppression model 105 of FIG. 1). The training device may be implemented as a separate device separated from a bone suppression apparatus (e.g., a bone suppression apparatus 100 of FIG. 1) and may be implemented as one device by being integrated with the bone suppression apparatus.

The training device may include a processor. The processor of the training device may obtain training data and may train the bone suppression model based on the obtained training data.

The training data for training the bone suppression model may include an image pair. The image pair may include a training input image and a ground truth output image mapped to the training input image. The training input image of the image pair may include an image where a bone in the captured area is represented, and the ground truth output image of the image pair may include an image where at least a portion of the bone of the training input image is suppressed.

The image pair of the training data of the bone suppression model may include a conversion image pair obtained by converting a planar computer tomography (CT) image pair (also represented as a CT image pair) obtained from a stereoscopic CT image.

The stereoscopic CT image may be an image reconfigured as a plurality of cross-sectional images are geometrically processed. The cross-sectional image may be obtained as a sinogram captured from all directions after an X-ray generator and an X-ray detector rotate in pairs with respect to the subject is restored through inverse Radon transform. A voxel value of each voxel of the stereoscopic CT image may refer to an attenuation rate of the X-ray by at least one of a bone, an organ, tissue, water, fat, and air at a corresponding location. A pixel value of each pixel of the cross-sectional image may refer to an attenuation rate of the X-ray by at least one of a bone, an organ, tissue, water, fat, and air at a corresponding location.

A planar CT image may be obtained by projecting the stereoscopic CT image onto a projection surface. The projection plane may illustratively include at least one of a coronal plane, a sagittal plane, and an axial plane. However, the inventive concept is not limited thereto. The projection plane may include a plane which is present on a three-dimensional (3D) space. The planar CT image may be obtained by projecting the stereoscopic CT image by illustratively using a digitally reconstructed radiograph (DRR) method. The DRR method may indicate a projection technique for obtaining the planar CT image from the stereoscopic CT image.

In operation 210, the processor of the training device may obtain a CT image pair. The CT image pair may include a basic CT image and a suppression CT image where at least a portion of a bone of the basic CT image is suppressed. The processor of the training device may obtain the CT image pair from a basic stereoscopic CT image. The obtaining of the CT image pair will be described below with reference to FIG. 3.

In operation 220, the processor of the training device may convert the CT image pair into a conversion image pair. The conversion image pair may include a basic conversion image and a suppression conversion image where at least a portion of a bone of the basic conversion image is suppressed. The processor of the training device may apply a style conversion model to the CT image pair to obtain the conversion image pair.

The style conversion model may include a machine learning model learned to output a conversion image pair by being applied to a planar CT image pair. The conversion image may include an image having a style of a simple X-ray image. The acquisition of the conversion image pair using the style conversion model will be described below with reference to FIG. 4.

In operation 230, the processor of the training device may train the bone suppression model based on the training data of the bone suppression model. The processor of the training device may perform supervised learning by respectively using the basic conversion image and the suppression conversion image of the conversion image pair of the training data as a training input and a ground truth. The training by means of the supervised learning of the bone suppression model will be described below with reference to FIG. 6.

According to the training operation of the bone suppression model according to the inventive concept, for pediatrics as well as an adult, an image pair including a training input image and a ground truth output image mapped to the training input image may be obtained.

The bone suppression model according to the inventive concept may include a machine learning model for processing a pediatric simple X-ray input image for pediatrics. For training by means of the supervised learning of the bone suppression model, training data of the bone suppression model may be required to include the image pair including the training input image and the ground truth output image mapped to the training input image. However, as described above with reference to FIG. 1, because it is impossible to obtain a simple X-ray image for pediatrics through a dual energy X-ray, it may be difficult to obtain a simple X-ray image for the pediatrics and a simple X-ray image where at least a portion of a bone of the simple X-ray image for the pediatrics is suppressed.

In operations S210, 220, and 230, the processor of the training device may fail to obtain a simple X-ray image where at least a portion of a bone is suppressed from a simple X-ray image where the bone is represented. Instead, the processor of the training device may obtain a CT image pair including a basic CT image and a suppression CT image for pediatrics from a stereoscopic CT image for the pediatrics. Thereafter, the processor of the training device may convert the obtained CT image pair for pediatrics to obtain a conversion image pair for the pediatrics. For example, the processor of the training device may apply a style conversion model to the CT image pair for pediatrics to convert the CT image pair for the pediatrics into a conversion image pair for the pediatrics. Because the basic simple X-ray image is unable to be directly converted into a suppression simple X-ray image, even when it is impossible to obtain a simple X-ray image through a dual energy X-ray (e.g., when a patient is pediatrics), the processor of the training device may obtain an image pair including a training input image and a ground truth output image.

Figure 3:
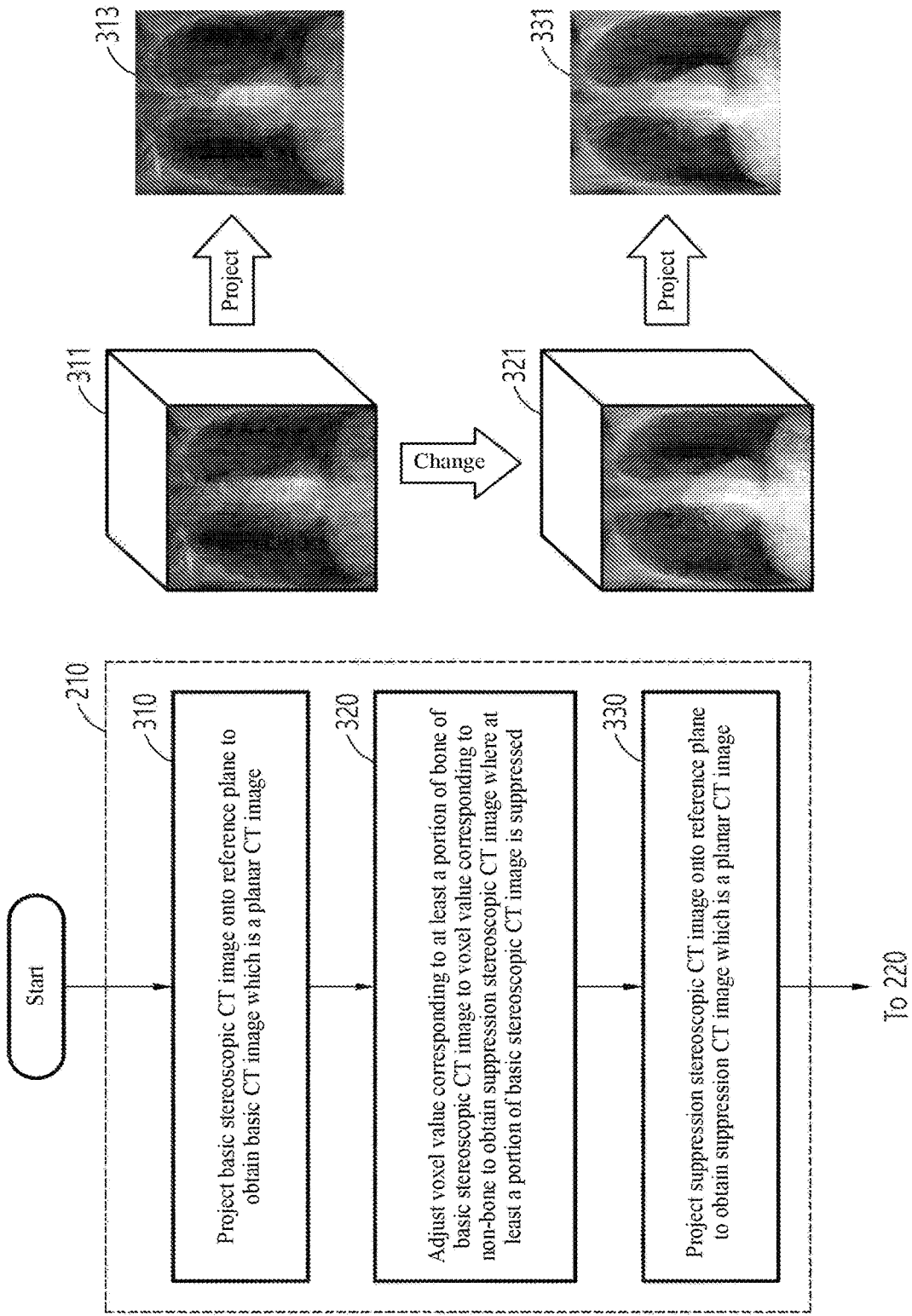
FIG. 3 illustrates acquisition of a CT image pair according to the inventive concept.

FIG. 3 illustrates acquisition of a CT image pair according to the inventive concept.

A training device according to the inventive concept may obtain a CT image pair. The CT image pair may include a basic CT image 313 and a suppression CT image 331.

The basic CT image 313 may be a planar CT image, which may indicate a planar CT image obtained by projecting a basic stereoscopic CT image 311 onto a reference plane. The suppression CT image 331 may be a planar CT image, which may indicate a planar CT image where at least a portion of a bone of the basic CT image 313 is suppressed.

In operation 310, the processor of the training device may obtain the basic CT image 313 from the basic stereoscopic CT image 311.

The basic stereoscopic CT image 311 may indicate a stereoscopic CT image where a bone included in an area captured for a patient is represented. The basic CT image 313 may include a planar image obtained by projecting the basic stereoscopic CT image 311 onto a reference plane. The basic CT image 313 may indicate a planar CT image where all of bones of the basic stereoscopic CT image 311 are represented (e.g., where at least some of the bones are not suppressed).

In operation 320, the processor of the training device may obtain a suppression stereoscopic CT image 321 from the basic stereoscopic CT image 311. The suppression stereoscopic CT image 321 may indicate a stereoscopic CT image where at least a portion of a bone of the basic stereoscopic CT image 311 is suppressed.

The processor of the training device may extract voxels corresponding to at least some of the bones of the basic stereoscopic CT image 311 from the basic stereoscopic CT image 311. The processor of the training device may extract a voxel having a voxel value which belongs to a threshold range as a voxel corresponding to the bone.

The processor of the training device may change voxel values of at least some of the extracted voxels to a voxel value corresponding to a non-bone (e.g., a voxel value which does not belong to the threshold range). The processor of the training device may change voxel values of at least some of the extracted voxels corresponding to the bones based on a voxel value of a voxel corresponding to a surrounding non-bone (e.g., a voxel corresponding to the non-bone within a threshold distance from the corresponding voxel).

The processor of the training device may change a voxel value corresponding to the bone to a voxel value corresponding to the non-bone to obtain the suppression stereoscopic CT image 321 where the bone of the basic stereoscopic CT image 311 is suppressed.

In operation 330, the processor of the training device may obtain the suppression CT image 331 from the suppression stereoscopic CT image 321. The suppression CT image 331 may include a planar image obtained by projecting the suppression stereoscopic CT image 321 onto the reference plane. The reference plane may be a plane such as a reference plane for obtaining the basic CT image 313. For example, the processor of the training device may project the basic stereoscopic CT image 311 onto a coronal plane to obtain the basic CT image 313 and may also project the suppression stereoscopic CT image 321 onto the coronal plane to obtain the suppression CT image 331.

Figure 4:
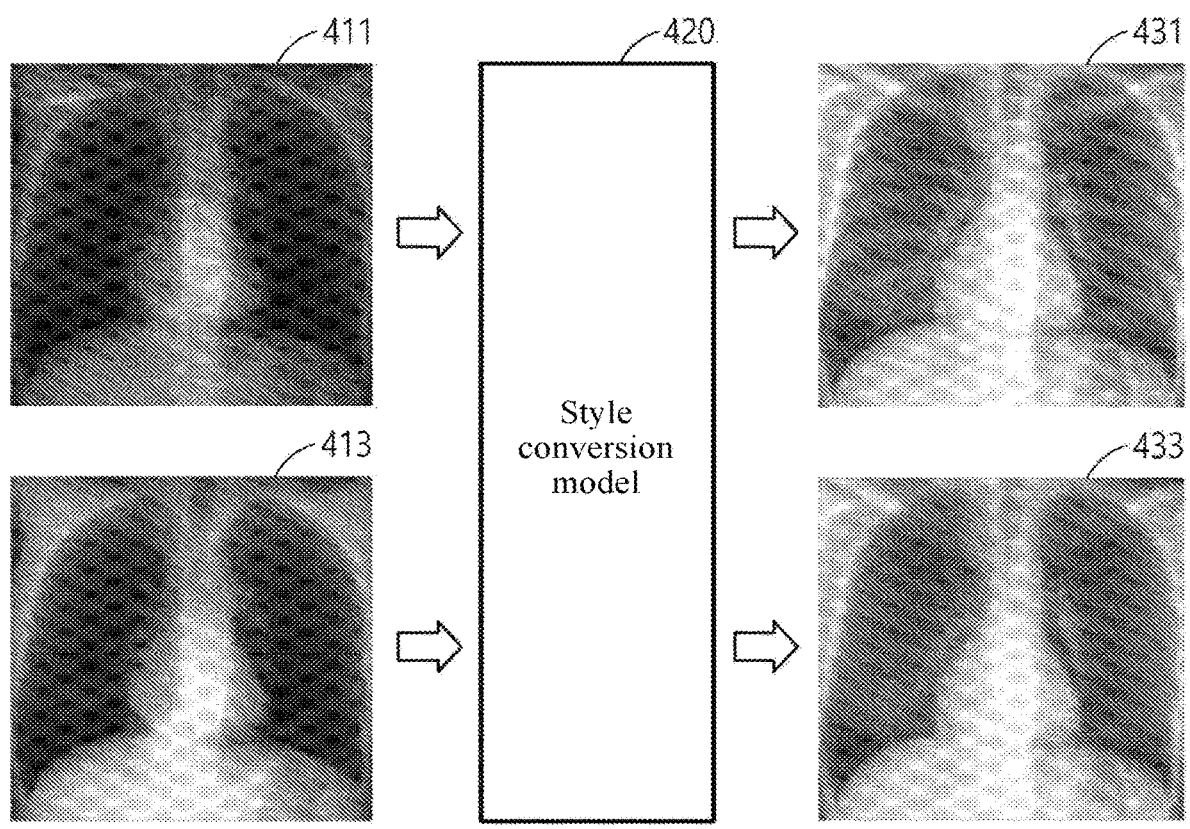
FIG. 4 illustrates acquisition of a conversion image pair according to the inventive concept.

FIG. 4 illustrates acquisition of a conversion image pair according to the inventive concept.

A training device according to the inventive concept may obtain a style conversion model 420 to a CT image pair to obtain a conversion image pair. The training device may convert the CT image pair into the conversion image pair using the style conversion model 420. As described above with reference to FIG. 2, the conversion image pair may be used as an image pair of training data of a bone suppression model.

The style conversion model 420 may be a model which converts a style while maintaining content of an image, which may include a machine learning model (e.g., a neural network) which generates an output image (e.g., a conversion image) pair of a simple X-ray image style from an input image pair of a planar CT image style. The input image pair and the conversion image pair may have different image styles while having content including a bone and an organ for the same patient. Style transfer of the image may be interpreted as image conversion from a domain (e.g., a planar CT domain) to which images of a planar CT image style belong to a domain (e.g., a simple X-ray domain) to which images of a simple X-ray image style belong.

The planar CT image style may indicate a visual style commonly indicated in planar CT images obtained by projecting a stereoscopic CT image. The visual style may be represented as texture, a pixel value, a color, and various elements of the image. The simple X-ray image style may refer to a visual style commonly indicated in simple X-ray images which are simply X-rayed. Illustratively, a range of pixel values of the planar CT image may be consistent for different patients. On the other hand, a range of pixel values of the simple X-ray image may vary for each patient. In other words, the distribution of the pixel values of the planar CT image may be similarly represented for several patients, but the distribution of the pixel values of the simple X-ray image may be variously represented for each patient. Thus, a range of pixel values of a conversion image generated based on the style conversion model 420 from an input image (e.g., a planar CT image) may be different from a range of pixel values of the input image. However, the example in which the distribution of the pixel values varies with the style conversion is mainly described for convenience of description, but not limited thereto. Different visual elements may also vary.

The style conversion model 420 according to the inventive concept may be learned according to contrastive unpaired translation (CUT). The CUT may indicate a learning scheme which updates a parameter of the style conversion model 420 using a loss (e.g., a contrastive loss and an adversarial loss) between corresponding portions in a training input image and an output image of the style conversion model 420. The style conversion model 420 may indicate a machine learning model trained based on training data including a plurality of planar CT images and a plurality of simple X-ray images. For example, the style conversion model 420 may be trained to output an image similar to a simple X-ray image by being applied to the planar CT image of the style conversion model 420.

The conversion image pair may include a basic conversion image 431 and a suppression conversion image 433.

The basic conversion image 431 may be an image having a simple X-ray image style, which may correspond to a basic CT image 411 of a CT image pair. The suppression conversion image 433 may be an image having a simple X-ray image style, which may correspond to a suppression CT image 413 of the CT image pair. A processor of the training device may apply the style conversion model 420 to the CT image pair of the basic CT image 411 and the suppression CT image 413 to convert the CT image pair into the conversion image pair including the basic conversion image 431 and the suppression conversion image 433. As described above, the basic CT image 411 may indicate a planar CT image where a bone is represented, and the suppression CT image 413 may indicate a planar CT image where at least a portion of the bone is suppressed.

The conversion image pair may not be a simple X-ray image obtained by simple X-ray capturing, but may be an image having a simple X-ray style to be used to train a bone suppression model. The bone suppression model may include a model which outputs a suppression simple X-ray image by being applied to a basic simple X-ray image. However, a training input image of the simple X-ray image and a ground truth output image of the simple X-ray image may not be necessarily required for training of the bone suppression model. The processor of the training device may train the bone suppression model using the conversion image pair having the simple X-ray style. The training of the bone suppression model using the conversion image pair will be described with reference to FIGS. 5 and 6.

Figure 5:
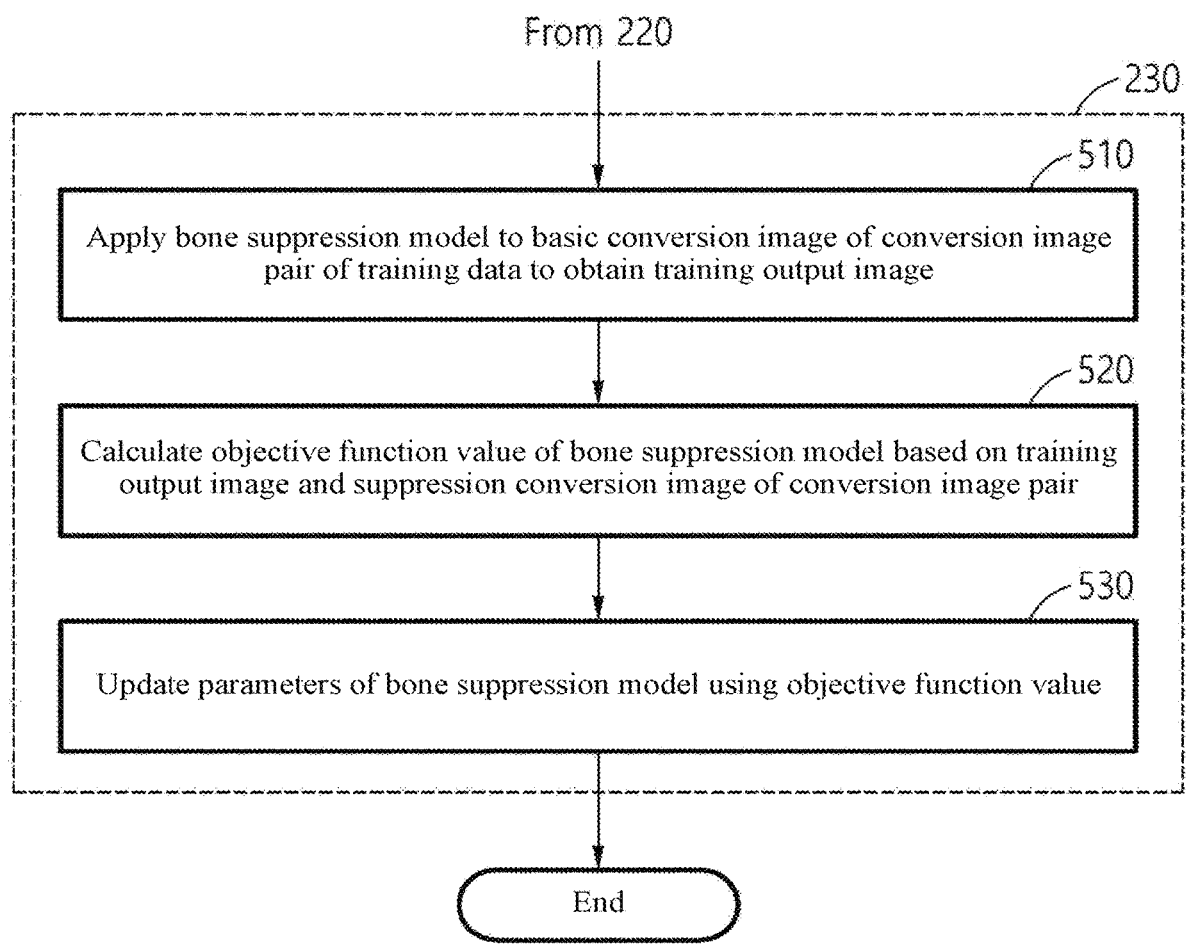
FIGS. 5 and 6 illustrate a training operation of a bone suppression model according to the inventive concept.
Figure 6:
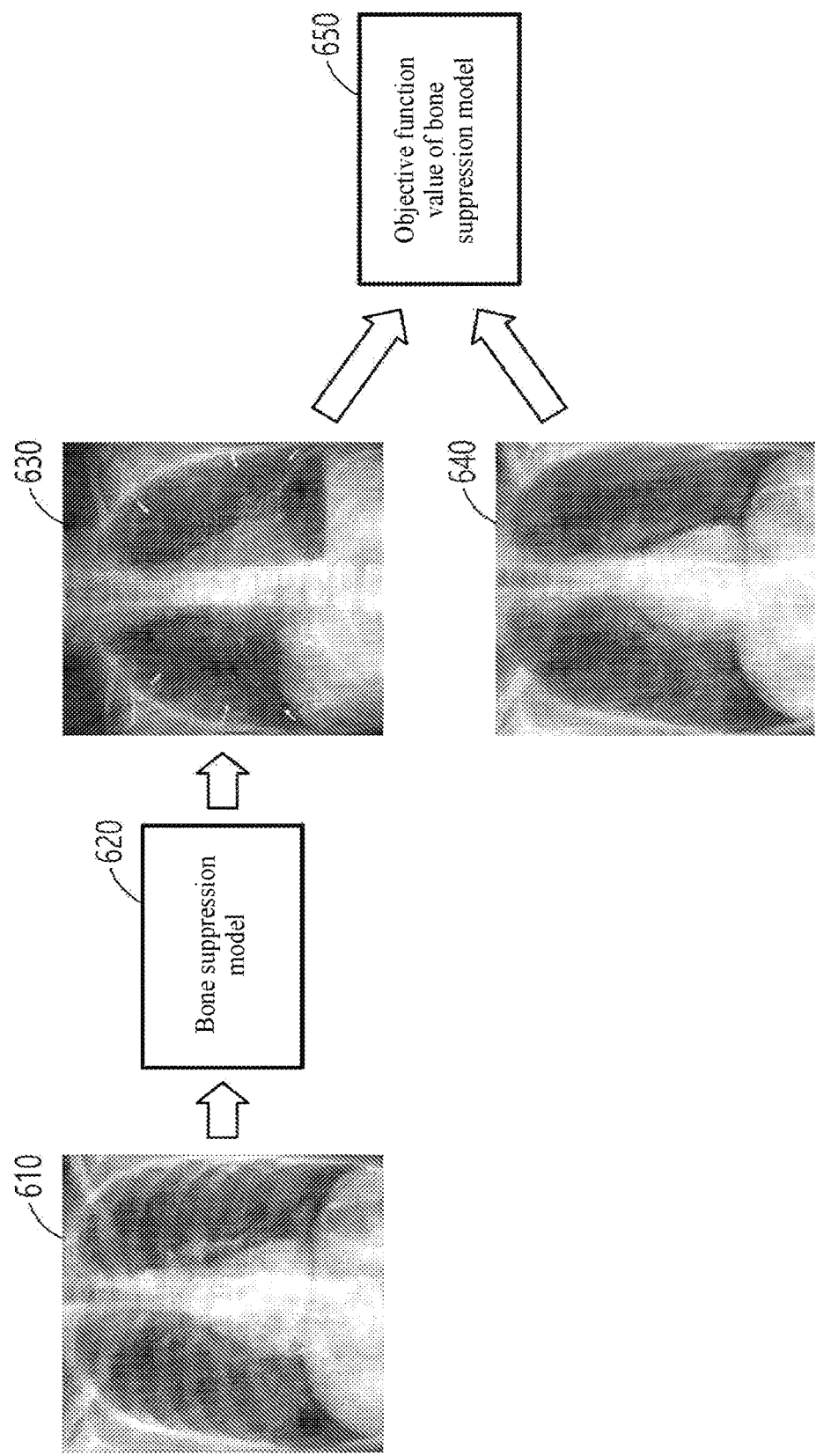

FIGS. 5 and 6 illustrate a training operation of a bone suppression model according to the inventive concept.

A processor of a training device according to the inventive concept may train a bone suppression model 620 based on training data of the bone suppression model 620. The training data may include a conversion image pair. The conversion image pair may include a basic conversion image 610 and a suppression conversion image 640 where at least a portion of a bone of the basic conversion image 610 is suppressed. The processor of the training device may use the basic conversion image 610 as a training input image and may use the suppression conversion image 640 as a ground truth output image to perform training by means of supervised learning.

In operation 510, the processor of the training device may apply the bone suppression model 620 to the simple conversion image 610 to obtain a training output image 630.

In operation 520, the processor of the training device may calculate an objective function value 650 of the bone suppression model 620 based on the training output image 630 and the suppression conversion image 640. The suppression conversion image 640 may be mapped to the basic conversion image 610.

The processor of the training device may calculate the objective function value 650 based on a pixel value difference between a pixel of the training output image 630 and a pixel of the suppression conversion image 640, which corresponds to the pixel of the training output image 630. Illustratively, as the pixel value difference between the training output image 630 and the suppression conversion image 640 increases, the calculated objective function value 650 may increase.

In operation 530, the processor of the training device may update parameters of the bone suppression model 620 using the objective function value 650.

When the calculated objective function value is greater than a threshold, the processor of the training device may repeat operations 510, 520, and 530. When the calculated objective function value is less than or equal to the threshold, the processor of the training device may complete the training of the bone suppression model 620. Thereafter, the processor of the training device may obtain the trained bone suppression model 620.

The above-described embodiments may be implemented with hardware components, software components, and/or a combination of hardware components and software components. For example, the devices, methods, and components described in the embodiments may be implemented in general-use computers or special-purpose computers, such as a processor, a controller, an arithmetic logic unit (ALU), a digital signal processor, a microcomputer, a field programmable array (FPGA), a programmable logic unit (PLU), a microprocessor, or any device which may execute instructions and respond. A processing unit may perform an operating system (OS) or a software application running on the OS. Further, the processing unit may access, store, manipulate, process and generate data in response to execution of software. It will be understood by those skilled in the art that although a single processing unit may be illustrated for convenience of understanding, the processing unit may include a plurality of processing elements and/or a plurality of types of processing elements. For example, the processing unit may include a plurality of processors or one processor and one controller. Also, the processing unit may have a different processing configuration, such as a parallel processor.

Software may include computer programs, codes, instructions or one or more combinations thereof and may configure a processing unit to operate in a desired manner or may independently or collectively instruct the processing unit. Software and/or data may be permanently or temporarily embodied in any type of machine, components, physical equipment, virtual equipment, computer storage media or units or transmitted signal waves so as to be interpreted by the processing unit or to provide instructions or data to the processing unit. Software may be dispersed throughout computer systems connected via networks and may be stored or executed in a dispersion manner. Software and data may be recorded in one computer-readable storage media.

The methods according to the embodiments may be implemented with program instructions which may be executed through various computer means and may be recorded in computer-readable media. The computer-readable media may include program instructions, data files, data structures, and the like alone or in combination, and the program instructions recorded on the media may be specially designed and configured for an embodiment or may be known and usable to those skilled in the art of computer software. Examples of computer-readable media include magnetic media such as hard disks, floppy disks, and magnetic tape; optical media such as compact disc-read only memory (CD-ROM) disks and digital versatile discs (DVDs); magneto-optical media such as floptical disks; and hardware devices that are specially configured to store and perform program instructions, such as read-only memory (ROM), random access memory (RAM), flash memory, and the like. Program instructions include both machine codes, such as produced by a compiler, and higher level codes that may be executed by the computer using an interpreter.

The above-described hardware devices may be configured to act as one or a plurality of software modules to perform the operations of the embodiments, or vice versa.

Even though the embodiments are described with reference to restricted drawings, it may be obviously to one skilled in the art that the embodiments are variously changed or modified based on the above description. For example, adequate effects may be achieved even if the foregoing processes and methods are carried out in different order than described above, and/or the aforementioned elements, such as systems, structures, devices, or circuits, are combined or coupled in different forms and modes than as described above or be substituted or switched with other components or equivalents.

Therefore, other implements, other embodiments, and equivalents to claims are within the scope of the following claims.

What is claimed is:

1. A method performed by a processor of a medical image processing apparatus, the method comprising:
    obtaining a basic computer tomography (CT) image and a suppression CT image where at least a portion of a bone of the basic CT image is suppressed;
    applying a style conversion model to a CT image pair including the basic CT image and the suppression CT image to convert the CT image pair into a conversion image pair; and
    training a bone suppression model for a simple X-ray image based on training data including the conversion image pair,
    wherein the obtaining of the basic CT image and the suppression CT image includes:
    projecting a basic stereoscopic CT image onto a reference plane to obtain the basic CT image being a planar CT image; and
    projecting a suppression stereoscopic CT image onto the reference plane to obtain the suppression CT image being a planar CT image, the suppression stereoscopic CT image being obtained by changing a first voxel value corresponding to at least a portion of a bone of the basic stereoscopic CT image to a second voxel value corresponding to a non-bone, the at least a portion of the bone being a bone corresponding to a voxel having the first voxel value which belongs to a threshold range in the bone of the basic stereoscopic CT image, and the second voxel value being a value of a voxel corresponding to the non-bone within a threshold distance from a voxel having the first voxel value,
    wherein the training of the bone suppression model includes:
    applying the bone suppression model to a basic conversion image of the conversion image pair to obtain a training output image;
    calculating an objective function value of the bone suppression model based on the training output image and a suppression conversion image of the conversion image pair; and
    updating parameters of the bone suppression model using the objective function value,
    wherein the calculating of the objective function value includes:
    calculating the objective function value based on a pixel value difference between a first pixel of the training output image and a second pixel of the suppression conversion image, the second pixel corresponding to the first pixel, the objective function value being calculated as a large value as the pixel value difference increases, and
    wherein the obtaining of the training output image, the calculating of the objective function value, and the updating of the parameters are repeated to train the bone suppression model, until the objective function value is less than a predetermined threshold.

2. The method of claim 1, further comprising:
    applying the trained bone suppression model to a simple X-ray input image to obtain a simple X-ray output image where at least a portion of a bone of the simple X-ray input image is suppressed.

3. The method of claim 2, wherein the obtaining of the simple X-ray output image includes:
    applying the bone suppression model to the simple X-ray input image for pediatrics to obtain the simple X-ray output image where the at least a portion of the bone of the simple X-ray input image is suppressed.

4. The method of claim 1, further comprising:
    obtaining the CT image pair for pediatrics, the CT image pair including the basic CT image and the suppression CT image for the pediatrics.

5. The method of claim 1, wherein the converting into the conversion image pair includes:
    applying the style conversion model to the CT image pair for pediatrics to convert the CT image pair for the pediatrics into the conversion image pair for the pediatrics.

6. The method of claim 1, wherein the training of the bone suppression model includes:
    using a basic conversion image of the conversion image pair of the training data as a training input image and using a suppression conversion image of the conversion image pair as a ground truth output image to train the bone suppression model by means of supervised learning.

7. A computer-readable storage medium storing a program combined with hardware to execute the method of claim 1.

8. An apparatus, comprising:
    a processor configured to obtain a basic CT image and a suppression CT image where at least a portion of a bone of the basic CT image is suppressed, apply a style conversion model to a CT image pair including the basic CT image and the suppression CT image to convert the CT image pair into a conversion image pair, and train a bone suppression model for a simple X-ray image based on training data including the conversion image pair, wherein the processor is configured to:
project a basic stereoscopic CT image onto a reference plane to obtain the basic CT image being a planar CT image, when obtaining the basic CT image and the suppression CT image, and project a suppression stereoscopic CT image onto the reference plane to obtain the suppression CT image being a planar CT image, the suppression stereoscopic CT image being obtained by changing a first voxel value corresponding to at least a portion of a bone of the basic stereoscopic CT image to a second voxel value corresponding to a non-bone, the at least a portion of the bone being a bone corresponding to a voxel having the first voxel value which belongs to a threshold range in the bone of the basic stereoscopic CT image, and the second voxel value being a value of a voxel corresponding to the non-bone within a threshold distance from a voxel having the first voxel value;
apply the bone suppression model to a basic conversion image of the conversion image pair to obtain a training output image, when training the bone suppression model, calculate an objective function value of the bone suppression model based on the training output image and a suppression conversion image of the conversion image pair, and update parameters of the bone suppression model using the objective function value;
calculate the objective function value based on a pixel value difference between a first pixel of the training output image and a second pixel of the suppression conversion image, the second pixel corresponding to the first pixel, when calculating the objective function value, the objective function value being calculated as a large value as the pixel value difference increases; and
repeat the obtaining of the training output image, the calculating of the objective function value, and the updating of the parameters to train the bone suppression model, until the objective function value is less than a predetermined threshold.

9. The apparatus of claim 8, wherein the processor applies the trained bone suppression model to a simple X-ray input image to obtain a simple X-ray output image where at least a portion of a bone of the simple X-ray input image is suppressed.

10. The apparatus of claim 9, wherein the processor applies the bone suppression model to the simple X-ray input image for pediatrics to obtain the simple X-ray output image where the at least a portion of the bone of the simple X-ray input image is suppressed.

11. The apparatus of claim 8, wherein the processor obtains the CT image pair for pediatrics, the CT image pair including the basic CT image and the suppression CT image for the pediatrics.

12. The apparatus of claim 8, wherein the processor applies the style conversion model to the CT image pair for pediatrics to convert the CT image pair for the pediatrics into the conversion image pair for the pediatrics.

13. The apparatus of claim 8, wherein the processor uses a basic conversion image of the conversion image pair of the training data as a training input image and uses a suppression conversion image of the conversion image pair as a ground truth output image to train the bone suppression model by means of supervised learning.

* * * * *